United States Patent
Moskovitz

(10) Patent No.: US 12,274,484 B2
(45) Date of Patent: Apr. 15, 2025

(54) CRYOSURGICAL DEVICE AND MATERIALS AND METHOD OF USE THEREOF

(71) Applicant: Martin J. Moskovitz, West Orange, NJ (US)

(72) Inventor: Martin J. Moskovitz, West Orange, NJ (US)

(*) Notice: Subject to any disclaimer, the term of this patent is extended or adjusted under 35 U.S.C. 154(b) by 0 days.

(21) Appl. No.: 18/641,540

(22) Filed: Apr. 22, 2024

(65) Prior Publication Data

US 2024/0277394 A1 Aug. 22, 2024

Related U.S. Application Data

(63) Continuation-in-part of application No. PCT/US2023/062017, filed on Feb. 6, 2023.

(60) Provisional application No. 63/346,504, filed on May 27, 2022, provisional application No. 63/307,359, filed on Feb. 7, 2022.

(51) Int. Cl.
*A61B 18/02* (2006.01)
*A61B 18/00* (2006.01)

(52) U.S. Cl.
CPC .... *A61B 18/02* (2013.01); *A61B 2018/00464* (2013.01); *A61B 2018/00714* (2013.01); *A61B 2018/0293* (2013.01)

(58) Field of Classification Search
CPC ............... A61F 7/12; A61B 2018/0293; A61B 2018/00464
See application file for complete search history.

(56) References Cited

U.S. PATENT DOCUMENTS

| | | |
|---|---|---|
| 5,776,193 A | 7/1998 | Kwan et al. |
| 7,351,798 B2 | 4/2008 | Margolin et al. |
| 7,874,167 B2 | 1/2011 | Kammer et al. |
| 8,505,315 B2 | 8/2013 | Kasza et al. |
| D765,835 S | 9/2016 | Kammer et al. |
| D765,836 S | 9/2016 | Kammer et al. |
| 9,549,843 B2 | 1/2017 | Kammer et al. |
| 9,561,895 B1 | 2/2017 | Kammer et al. |

(Continued)

FOREIGN PATENT DOCUMENTS

| | | |
|---|---|---|
| WO | WO 2021/164578 A8 | 8/2021 |
| WO | WO 2021/195582 A1 | 9/2021 |

(Continued)

OTHER PUBLICATIONS

Braz et al., Mortality in Anesthesia: A Systemic Review, Clinics 2009;64(10) 999-1006.

(Continued)

*Primary Examiner* — Kaitlyn E Smith
(74) *Attorney, Agent, or Firm* — Mark S. Cohen; PEARL COHEN ZEDEK LATZER BARATZ LLP

(57) ABSTRACT

Provided in the present disclosure are materials, devices, systems, and methods for performing cryo-surgery in a mammalian subject. More particularly, presented are a slurry, devices, systems, and methods for subcutaneously injecting the slurry into a patient in need of bodyfat reduction intervention. The slurry, devices, systems, and methods permit highly efficacious subcutaneous ice phase-change lipolysis while not requiring that the patient be placed under general anesthesia, nor requiring significant new surgical training among practitioners.

6 Claims, 12 Drawing Sheets

(56) References Cited

U.S. PATENT DOCUMENTS

| | | |
|---|---|---|
| 9,693,892 B1 | 7/2017 | Kammer et al. |
| 9,980,765 B2 | 5/2018 | Avram et al. |
| 10,231,866 B1 | 3/2019 | Kammer et al. |
| 10,575,984 B2 | 3/2020 | Kammer et al. |
| 10,582,960 B2 | 3/2020 | Avram et al. |
| 10,646,666 B2 | 5/2020 | Cohn et al. |
| 11,241,330 B1 | 2/2022 | Sabir et al. |
| 11,399,882 B2 | 8/2022 | Stefater, III et al. |
| 11,471,401 B2 | 10/2022 | Garibyan et al. |
| 11,564,830 B2 | 1/2023 | Garibyan et al. |
| 11,819,451 B2 | 11/2023 | Kammer et al. |
| 2007/0056313 A1* | 3/2007 | Kasza .................. A61F 7/0085 62/353 |
| 2012/0000217 A1 | 1/2012 | Gudnason |
| 2015/0098903 A1 | 4/2015 | Elmaleh et al. |
| 2016/0175141 A1* | 6/2016 | Wu .......................... A61F 7/12 607/105 |
| 2017/0274011 A1 | 9/2017 | Garibyan et al. |
| 2021/0030457 A1 | 2/2021 | Avram et al. |
| 2021/0244817 A1* | 8/2021 | Garibyan ............. A61K 31/245 |
| 2021/0322084 A1 | 10/2021 | Velis et al. |
| 2021/0346192 A1* | 11/2021 | Velis .................... A61K 9/0019 |
| 2021/0386580 A1* | 12/2021 | Velis .................... B01F 27/1142 |
| 2022/0273560 A1 | 9/2022 | Sabir et al. |
| 2022/0273569 A1 | 9/2022 | Anderson et al. |
| 2022/0313477 A1 | 10/2022 | Sabir et al. |
| 2022/0379071 A1 | 10/2022 | Stefater, III et al. |
| 2023/0363940 A1 | 11/2023 | Garibyan et al. |
| 2024/0058166 A1 | 2/2024 | Kammer et al. |

FOREIGN PATENT DOCUMENTS

| | | |
|---|---|---|
| WO | WO 2022/055934 A1 | 3/2022 |
| WO | WO 2022/211904 A1 | 10/2022 |
| WO | WO 2023/278891 A1 | 1/2023 |
| WO | WO 2023/034390 A1 | 3/2023 |

OTHER PUBLICATIONS

Ingargiola et al., Cryolipolysis for Fat Reduction and Body Contouring: Safety and Efficacy of Current Treatment Paradigms. Plast and Reconst Surg, Jun. 2015 135(6) 1581-90.).

International Search Report from PCT/US23/62017 dated Jul. 31, 2023.

Kandula et al., Injection Cryolipolysis: First-in-Human Study. Plast Reconstr Surg Glob Open Sep. 2021;9(9): e3818.

Rochon et al., A systematic review of the evidence for hypodermoclysis to treat dehydration in older people, J Gerontol A, May 1997; 52(3):M169-76.

Sasaki et al., Noninvasive Selective Cryolipolysis and Reperfusion Recovery for Localized Natural Fat Reduction and Contouring, Aesthetic Surg J, 34(3) 420-31 (2014).

Turner et al. Subcutaneous dextrose for rehydration of elderly patients—an evidence-based review, B.M.C. Geriatr 2004; 4(2).

Zelickson et al. (2009). Cryolipolysis for noninvasive fat cell destruction: initial results from a pig model. Derma Surg, 35(10), 1462-70.

Zocchi M., Clinical Aspects of Ultrasonic Liposculpture, Semin Plast Surg 1993 7(2): 153-72. (Abstract).

International Preliminary Report on Patentability from PCT/US23/62017 dated Aug. 22, 2024.

Written Opinion from PCT/US23/62017 dated Jul. 31, 2023.

* cited by examiner

Insert sterile ice slurry using slurry production container

CRYOSURGICAL DEVICE AND MATERIALS AND METHOD OF USE THEREOF

CROSS-REFERENCE TO RELATED APPLICATION

This application is a Continuation-in-Part of International Application PCT/US2023/062017, filed Feb. 6, 2023, which claims priority from U.S. Provisional Application No. 63/307,359 filed Feb. 7, 2022, and U.S. Provisional Application No. 63/346,504 filed May 27, 2022, the contents of each of which are hereby incorporated by reference in their entireties.

FIELD OF THE INVENTION

The present disclosure relates to the field of surgical devices, materials, and methods. More particularly, the present disclosure provides devices, materials, and methods for performing injection ice phase-change lipolysis.

BACKGROUND OF THE INVENTION

Bodyfat reduction interventions are incredibly popular and a significant source of revenue for medical practitioners and medical supply manufacturers. For the year 2019, the American Society of Plastic Surgeons reported over 265,000 liposuction operations.

Bodyfat interventions include changes and improvements to diet; improved exercise habits; nutritional supplements; drugs; and micro-and macro-surgeries, including, for example, lap band, gastric balloon, liposuction, lipectomy, and the like. Each of these interventions carries certain disadvantages, including high patient cost, pain, discomfort, unwanted side effects, health risks, inconvenience, time commitment, and poorer-than-desired effectiveness.

Consequently, there is significant unmet need for a safe and effective bodyfat reduction intervention that can be performed at reasonable cost.

SUMMARY OF THE INVENTION

The present disclosure provides surgical materials, surgical devices, systems, and methods of use thereof. More particularly, the present disclosure provides devices, materials, and methods for performing injection ice phase-change lipolysis in a mammalian subject in need thereof.

In an aspect, the present disclosure provides a slurry for use in surgery in a mammalian subject comprising a mixture of chilled aqueous solution and ice, wherein the aqueous solution comprises dissolved simple carbohydrates and dissolved salt. In any embodiment of the slurry, the simple carbohydrate may comprise any monosaccharides having between 3 and 7 carbon atoms. In some embodiments, the simple carbohydrate may comprise any monosaccharides having 6 carbon atoms. In still further embodiments, the simple carbohydrate consists of dextrose.

It will be appreciated that herein the specification and appended claims, unless otherwise indicated from context, the term "slurry" refers to a mixture of a chilled liquid, such as an aqueous solution, and ice. Typically, such a slurry will be at a low temperature, for example less than about 0° C.

In any embodiment of the slurry, the salt may comprise a biocompatible salt. In some embodiments, the salt may be a chloride salt. In some embodiments, the salt consists of sodium chloride.

In some embodiments of the slurry, the simple carbohydrate is dextrose and the salt is sodium chloride, both in aqueous solution, in sufficient concentrations such that the slurry may be super-chilled while remaining substantially free-flowing liquid solution.

In any embodiment of the slurry, the slurry may be sterile. In any embodiment of the slurry, the slurry may be sterile.

In another aspect, the present description provides a surgical injection device comprising a container operably coupled to a surgical pump, wherein the container is operably coupled to or further comprises a mixing means. The mixing means may comprise one or more mix pumps or an internal auger. In any embodiment of the surgical injection device, the container may contain a slurry, which may comprise a mixture of chilled aqueous solution and ice, wherein the aqueous solution comprises dissolved simple carbohydrates and dissolved salt. In some embodiments of the surgical injection device, the surgical pump may comprise a peristaltic roller pump.

In any embodiment of the surgical injection device, the device may further comprise a cannula/instillation needle, the needle operably coupled to the surgical pump. In some embodiments, the needle is a 2.7 mm OD needle.

In any embodiment of the surgical injection device, the hopper may further comprise a lid enclosing the container.

In another aspect, the present disclosure provides a surgical injection system, the system comprising a container, wherein the container is configured to receive and contain slurry; a surgical pump operably coupled to the container; and a cannula/instillation needle operably coupled to the surgical pump; wherein the slurry comprises a chilled aqueous solution and ice, wherein the aqueous solution comprises dissolved monosaccharide and dissolved salt. In any embodiment of the system, the container may comprise a mix funnel. In any such embodiment, the mix funnel may comprise an upper portion and a lower tip portion. In such embodiments, the upper portion may comprise one or more hook-ups for tubing. The mix funnel may be fluidically coupled to one or more mix pumps, which may circulate and maintain the liquid: ice ratio and/or constituency of the slurry.

In some embodiments of the surgical injection system, the monosaccharide is dextrose and the salt is sodium chloride. In some embodiments, the system is capable of effective operation at supercooled temperatures. In some embodiments, the slurry is at a sufficiently cold temperature such that the slurry can cause ice phase-change lipolysis when injected and contacted with live mammalian fat cells.

In any embodiment of the surgical injection system, the container may be refrigerated. In some embodiments, the container may be refrigerated at about 0° C. Any embodiment of the surgical injection system may further comprise a hold chamber. In any such embodiment, the hold chamber may be refrigerated. In some embodiments, the hold chamber may be refrigerated at about 0° C. The hold chamber may be configured to receive and hold batches of liquid solution and/or batches of slurry. In some embodiments, the hold chamber may comprise one or more containers having sidewalls comprising a Teflon™ material.

In another aspect, the present disclosure provides a method of causing injection ice phase-change lipolysis in a mammalian subject comprising the steps of: subcutaneously injecting a slurry such that the slurry comes into proximity with fat cells to be ice-phase-lipolysed, wherein the slurry comprises a mixture of chilled aqueous solution and ice, wherein the aqueous solution comprises dissolved simple carbohydrates and dissolved salt.

In some embodiments, the dissolved simple carbohydrates consist of dextrose and dissolve salt consists of sodium chloride.

In any embodiment of the method, the method may be performed using the devices and systems provided in the present disclosure. In any embodiment of the method, the method may be performed using sterile devices and materials, and aseptic techniques.

According to an aspect of the presently disclosed subject matter, there is provided an aqueous solution comprising a dissolved monosaccharide and a dissolved salt, the dissolved monosaccharide and salt being of sufficient concentration such that the aqueous solution becomes a slurry of chilled aqueous solution and ice when cooled to a temperature of or below about −1.5° C. while remaining a substantially free-flowing liquid solution mixture.

The dissolved monosaccharide and salt may be of sufficient concentration such that the aqueous solution becomes a slurry when cooled to a temperature of or below about −1.7° C. while remaining a substantially free-flowing liquid solution mixture.

The concentration of the monosaccharide may be no less than about 12.2 wt %, with the concentration of the salt being no greater than about 0.18 wt %.

The monosaccharide may have between 3 and 7 carbon atoms.

The monosaccharide may have 6 carbon atoms.

The monosaccharide may be dextrose.

The salt may be a biocompatible salt.

The salt may be sodium chloride.

The monosaccharide may be dextrose, and the salt may be sodium chloride.

According to another aspect of the presently disclosed subject matter, there is provided a surgical injection device comprising:
   a container configured to contain a slurry therewithin; and
   a surgical pump operably coupled to the container to facilitate administering the slurry from the container to a patient via a patient tube,
wherein the container comprises a mixing means configured to agitate the slurry so as to maintain a predetermined liquid-ice ratio and/or consistency.

The mixing means may comprise one or more mixing tubes each attached to the container at both ends, and a mixing pump associated with each of the tubes and configured to circulate slurry from the container through the mixing tubes, thereby providing the agitation.

The surgical injection device may comprise two or more mixing tubes and two or more mixing pumps, each associated with one of the tubes.

Each of the mixing pumps may comprise a peristaltic pump.

The container may have a downwardly tapering shape, wherein one end of each of the mixing tubes is attached to the container at a lower end thereof.

The mixing means may comprise an augur internal to the container.

The surgical pump may comprise a peristatic roller pump.

The surgical injection device may further comprise an instillation needle operably coupled to the surgical pump via the patient tube.

The surgical injection device may further comprise a lid for closing the container.

The slurry may be a mixture of chilled aqueous solution and ice, wherein the aqueous solution comprises a dissolved monosaccharide and a dissolved salt.

The dissolved monosaccharide and salt may be of sufficient concentration such that the aqueous solution becomes a slurry when cooled to a temperature of or below −1.5° C. while remaining a substantially free-flowing liquid solution mixture.

The monosaccharide may be dextrose and the salt may be sodium chloride.

The surgical injection device may be configured to administer the slurry at a sufficiently cold temperature suitable for ice phase-change lipolysis when in contact with live mammalian fat cells.

The container may be substantially surrounded by a cooling element, the cooling element being configured to maintain the contents of the container at an operating temperature.

The surgical injection device may further comprise a refrigerated hold chamber configured to receive therewithin one or more containers comprising aqueous solution and/or slurry, and to maintain them at a predefined cold temperature.

According to another aspect of the presently disclosed subject matter, there is provided a method of causing ice phase-change lipolysis in a mammalian subject, the method comprising subcutaneously injecting a slurry of chilled aqueous solution and ice such that the slurry comes into proximity with fat cells to be ice phase-change lipolysed, the slurry being made by cooling the aqueous solution described above to a temperature no greater than about −1.5° C.

The dissolved monosaccharide and salt may be of sufficient concentration such that the aqueous solution becomes the slurry when cooled to a temperature of or below about −1.5° C. while remaining a substantially free-flowing liquid solution mixture.

The monosaccharide may be dextrose and the salt may be sodium chloride.

The injection may be performed using the surgical injection device described in the previous aspect.

The slurry may be injected at a temperature between about −0.5° C. and about −1.7° C.

BRIEF DESCRIPTION OF THE FIGURES

Some embodiments are herein described, by way of example only, with reference to the accompanying figures. With specific reference now to the drawings in detail, it is stressed that the particulars shown are by way of example and for purposes of illustrative discussion of embodiments. In this regard, the description taken with the drawings makes apparent to those skilled in the art how embodiments may be practiced.

It should be readily understood from context that certain terms or labels may be interchangeable or synonymous. For example, a diagram depicting an element labeled "jar" may refer to a technical feature of the apparatus of the present disclosure which may be otherwise described herein as a "hopper".

FIG. 3A is a photograph depicting the insertion of an augur into a container. The augur, powered by, e.g., an electric motor, rotates, and thereby mixes ice slurry in the jar, maintaining the slurry in quasi-liquid state and preventing the slurry from separating into ice and liquid. FIG. 3B is a photograph depicting the container being filled with sterile ice slurry. FIG. 3C is a photograph depicting the container being enclosed by a lid.

FIG. 4A depicts excised untreated negative-control fat tissue. FIG. 4B depicts excised fat tissue treated with 300 cc-500 cc sterile ice slurry at about 0° C.

FIG. 5A depicts an illustration of an embodiment of an injection device having no touchscreen. FIG. 5B depicts an illustration of alternative embodiment of an injection device having an interactive touchscreen.

DETAILED DESCRIPTION OF THE INVENTION

Figure 1:
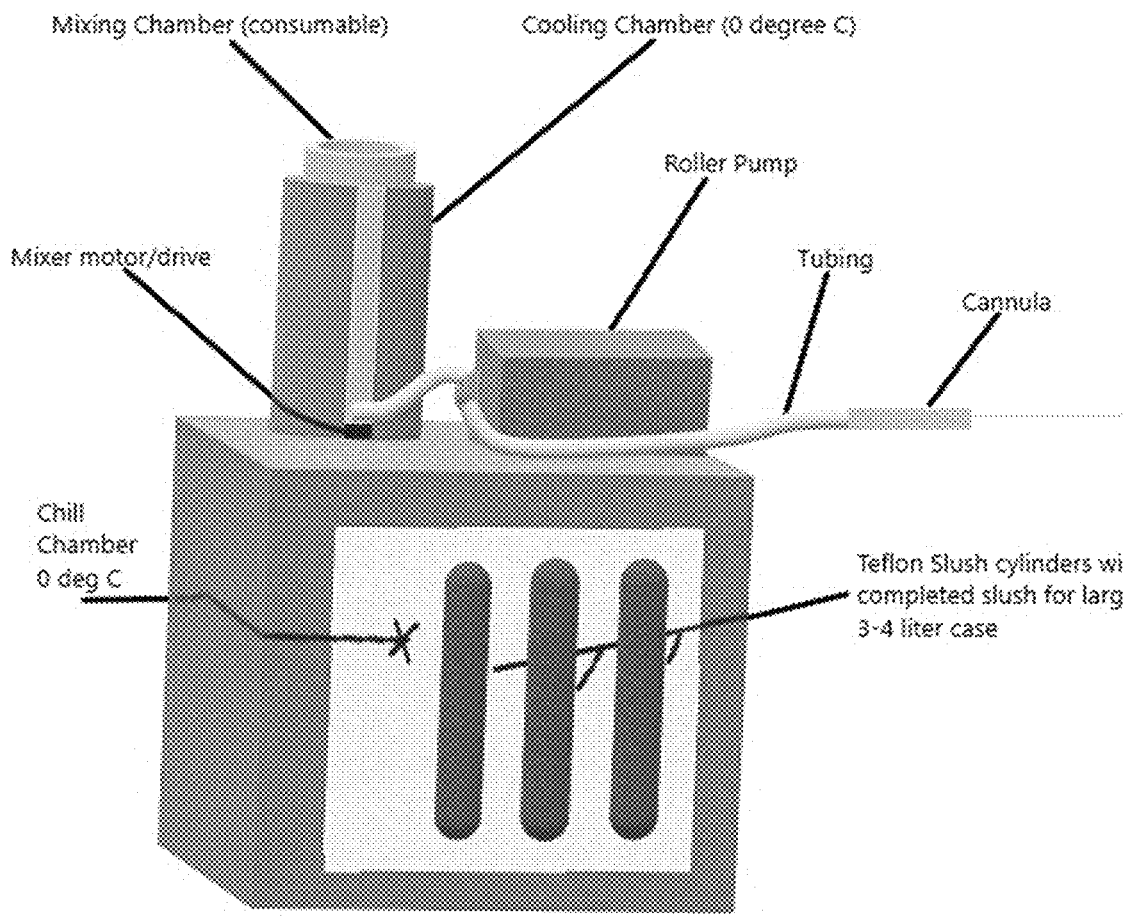
FIG. 1 depicts a schematic diagram of an embodiment of the surgical devices and systems of the present description. The device embodiment depicted in the schematic comprises a "hold chamber" for maintaining one or more batches of slurry at a cryogenic operating temperature, e.g., 0° C.; a mixing chamber, which may house a mixing means, such as an augur, for containing and mixing a new batch of consumable slurry; a cooling chamber surrounding the mixing chamber; a roller pump for advancing slurry through tubing to an instillation needle opening/cannula; and a cannula/needle, configured for subcutaneous insertion in a surgical patient. The inclusion of a "hold chamber" together with a "mixing chamber" permits keeping a batch of slurry cold while concurrently mixing another batch of slurry. Using the embodiment of FIG. 1, each batch of slurry may take approximately 50 minutes to make.
Figure 2:
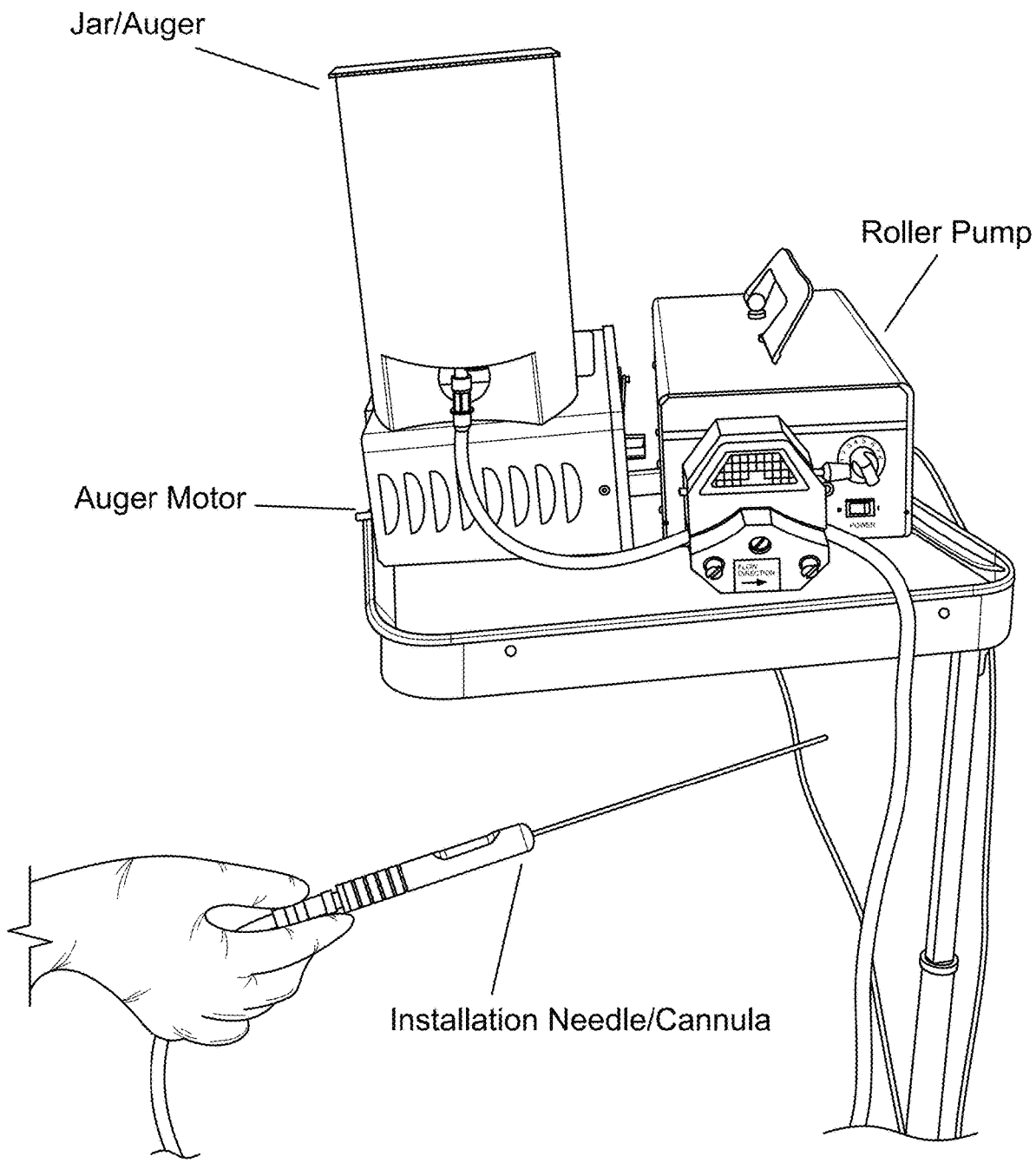
FIG. 2 is a photograph of a mockup of an embodiment of the surgical devices and systems of the present description. Pictured are a container having a mixing means, such as an augur operationally coupled to an augur motor, the container feeding into a tube. The tubing is operationally coupled to a roller pump, which may feed slurry through the tubing toward an instillation needle/cannula, for subcutaneously injecting slurry into a surgical patient.
Figure 3A:
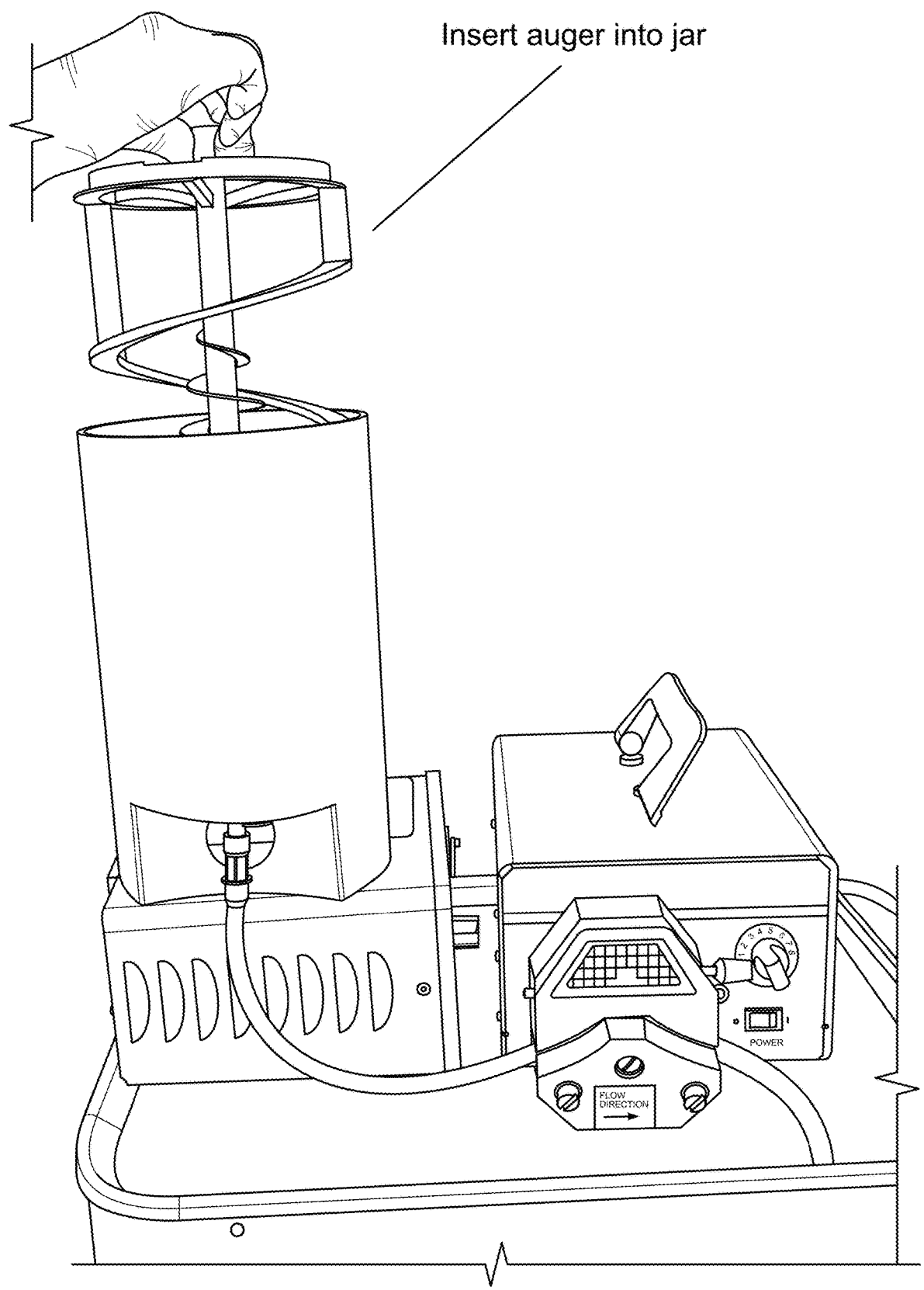
FIGS. 3A-3C are photographs depicting a progression of a method of using an embodiment of the surgical devices and systems of the present description.
Figure 3B:
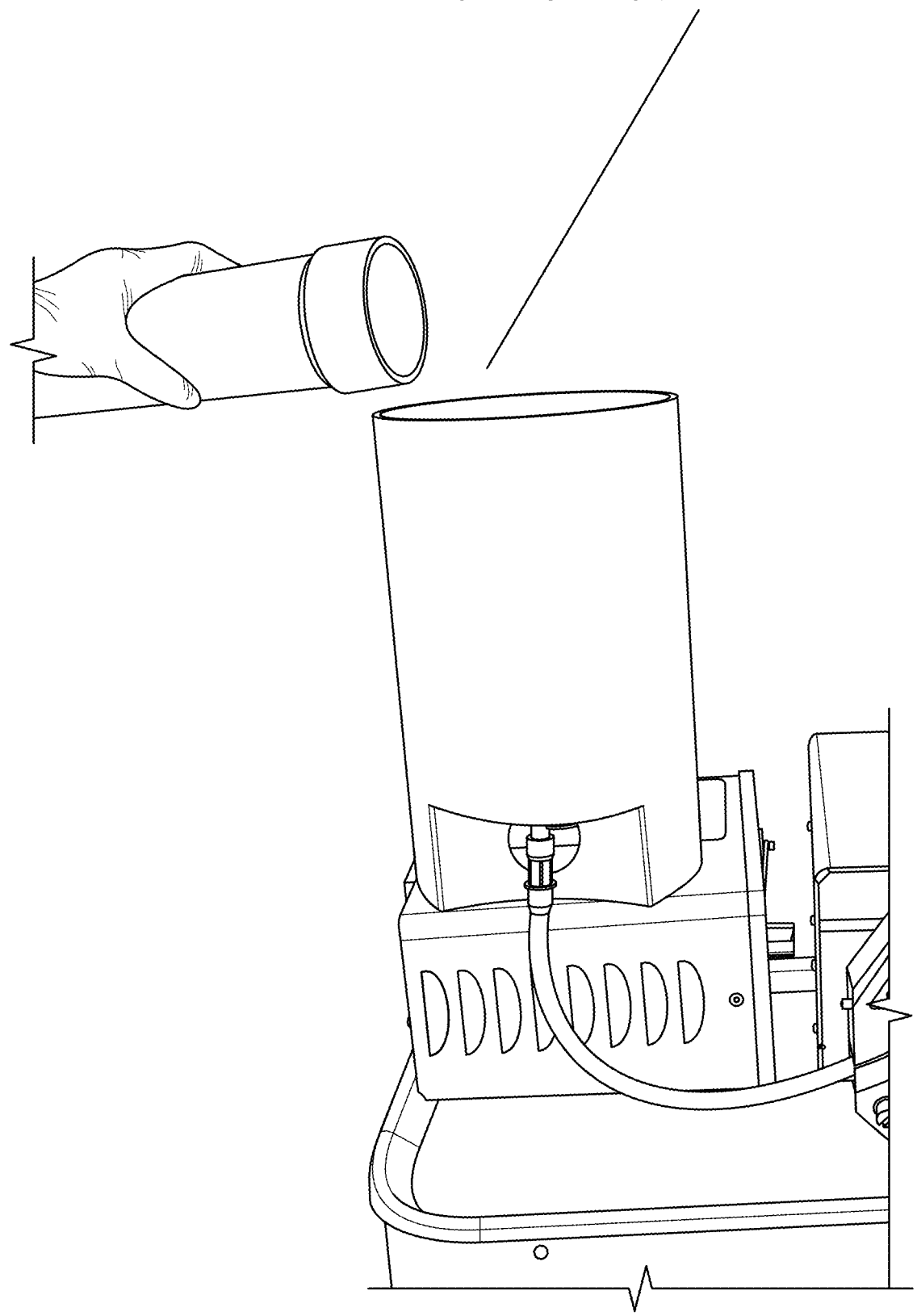
Figure 3C:
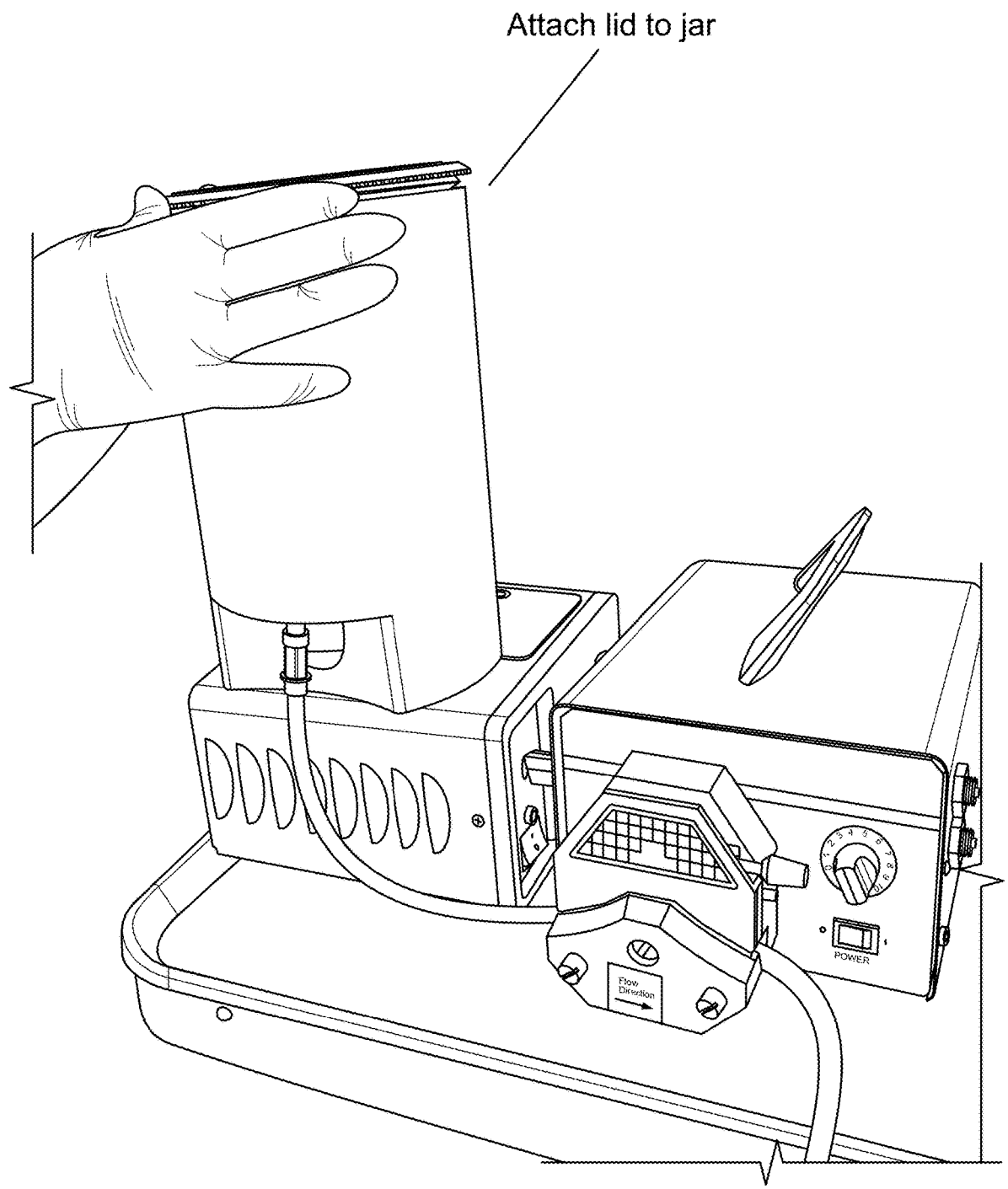

The presently described invention comprises surgical materials, a surgical device, materials, and methods of use thereof. More particularly, the present disclosure provides devices, materials, systems, and methods for performing injection ice phase-change lipolysis in a mammalian subject in need thereof.

Bodyfat reduction procedures such as traditional liposuction are highly popular—in recent years, surgeons have performed around 265,000 liposuction procedures per annum. Most liposuction operations are conducted under general anesthesia, which presents significant costs, equipment and staffing complexities, and medical risks as compared with local anesthesia methods, such as, e.g., tumescent anesthesia. General anesthesia is the riskiest aspect of surgeries in which it is used. A review from 2009 found that approximately 1 in 10,000 surgical patients who undergo general anesthesia die from general anesthesia related complications. See Leandro Gobbo Braz et al., *Mortality in Anesthesia: A Systemic Review*, CLINICS 2009;64(10) 999-1006 (2009). In other words, traditional liposuction carries all the risks and costs inherent to any invasive surgery.

Meanwhile, alternative nonsurgical approaches to traditional liposuction have emerged that target physical properties unique to lipids, permitting selective destruction of fat. Methods of devices in this technology area include those using ultrasonic, radio, and lasers. (See, e.g., Zocchi M., *Clinical Aspects of Ultrasonic Liposculpture*, SEMIN PLAST SURG 1993 7(2): 153-72.) Since around 2010,a method of cryolipolysis has become the most popular less-invasive or "non-invasive" alternative sculpting procedure that emerged from observations that fat-rich tissue was more susceptible than fat-poor tissue to cold injury. (See, e.g., Zelickson B., et al. (2009). *Cryolipolysis for noninvasive fat cell destruction: initial results from a pig model*. DERMA SURG, 35(10), 1462-70.) Subcutaneous fat can be reduced to a temperature causing cell death, while dermal tissues and subcutaneous muscle and connective tissues are unharmed. Then the patient's body simply excretes the dead fat cells.

"Ice phase-change lipolysis", as used throughout this disclosure (unless another meaning is clearly specified or implied in context) may refer to any method of using ice slurry injection to cause a cold temperature to achieve intentional targeted killing of a live animal's fat cells. "Cryolipolysis", as used throughout this disclosure (unless another meaning is clearly specified or implied in context) may refer to the transcutaneous application of cooling to achieve a cold temperature in order to achieve the intentional targeted killing of a live animal's fat cells.

Conventional cryolipolysis approaches elicit nonsurgical local fat reduction by contacting an applicator to a selected area, for a preset time, usually in 30-minute to 60-minute cycles. In conventional cryolipolysis, typically subcutaneous temperatures are lowered for about an hour to around 8° C. See Gordon H. Sasaki, MD, FACS et al., *Noninvasive Selective Cryolipolysis and Reperfusion Recovery for Localized Natural Fat Reduction and Contouring*, AESTHETIC SURG J, 34(3) 420-31 (2014). However, conventional cryolipolysis has, up to now, been less efficacious than liposuction. The method can be time consuming, and the locations and volumes of fat removal from the patient's body are limited.

Thus, patients seeking fat reduction interventions are caught between traditional liposuction (efficacious, but expensive, and requiring great expertise and general anesthesia) and conventional cryolipolysis (cheaper and not requiring general anesthesia, but less efficacious). The ice phase-change lipolysis materials, devices, systems, and methods of the present disclosure provide a unique solution to this dilemma without requiring significant new regulatory approvals or surgeon training.

Responding to these long-felt unmet needs, the present disclosure provides materials, systems, and methods for subcutaneous delivery of a sterile soft frozen ice slurry. The present disclosure provides systems and methods making use of ice phase-change lipolysis for achieving the disruption, absorption, and excretion of adipose cells, generally for the purpose of aesthetic body contouring (though the materials, systems, and methods may be used for other medical purposes). The materials, systems, and methods of the present disclosure enable the introduction of slurry into a patient's subcutaneous space in a process similar to tumescent solution placement in conventional liposuction. The melting ice slurry cools proximate fat cells through energy absorption, causing cell death. Thereafter, the lipid cell contents are absorbed by the patient's body and excreted. Such a system of the present disclosure may be indicated for use by a medical professional to make frozen saline for regional hypothermia in appropriate surgical or emergency procedures, and for transportation of transplant organs. The system of the present disclosure may be used when a patient is awake with no general anesthesia required. The systems and methods of the present disclosure are expected to provide an about 25% to about 50% reduction in fat in the treated areas.

The present disclosure provides a slurry that may be gently injected under a locally-anesthetized patient's dermis. The present disclosure further provides devices and systems and methods for injecting slurry to elicit bodyfat reduction. In 2021, a first-of-its-kind pilot study was published concluding that subcutaneous ice slurry injections are feasible, with an observed safety and tolerability profile comparable to that of topical cryolipolysis. (Kandula P. et al., *Injection Cryolipolysis: First-in-Human Study*. PLAST RECONSTR SURG GLOB OPEN 2021 September;9(9): e3818.) The injected subcutaneous ice slurry phase-change can induce ice phase-change lipolysis and is selective for the injected sites. No significant changes were observed in control sites. Thus, the present disclosure invention allows deeper, more efficacious fat reduction than conventional cryolipolysis without requiring general anesthesia, and without requiring significant regulatory approvals or practitioner training, since the methods of the present disclosure would be within the scope of most plastic surgeons' normal training and skillsets. Further, the present disclosed invention permits treatment in hard-to-reach areas on a patient's body.

The systems and methods of the present disclosure may be used to treat all localized subcutaneous fatty deposits for the purpose of aesthetic body contouring or other indicated medical purposes. Exemplary locations on a subject's body include submental, arms, chest, abdomen, flanks, torso, back, thighs, and legs. There is no specific body mass index (BMI) requirement indicated for use of the systems and methods of the present disclosure. A treatment using the systems and methods of the present disclosure may be expected to take about 10 to about 20 minutes. The subject's body area initially treated may be treated again if so desired. For example, a subject may have his thighs treated, and then several months later may have the same area treated again.

In an aspect, the present disclosure provides a slurry for use in surgery in a mammalian subject comprising a mixture of chilled aqueous solution and ice, wherein the aqueous solution comprises dissolved simple carbohydrates and dissolved salt.

In any embodiment of the slurry, the simple carbohydrate may comprise any monosaccharides having between 3 and 7 carbon atoms. In some embodiments, the simple carbohydrate may comprise any monosaccharides having 6 carbon atoms. In still further embodiments, the simple carbohydrate consists of dextrose.

In any embodiment of the slurry, the salt may comprise a biocompatible salt. In some embodiments, the salt may be a chloride salt. In some embodiments, the salt consists of sodium chloride.

Internal cryolysis methods have been used for treatment of tumors and other pathologies, but such methods reduce the local temperature to far below 0° C., and thus are not suited for fat-specific treatments. As stated above, conventional cryolipolysis methods in use since around 2010 involving applying cold temperature on the surface of the patient's skin. Meanwhile, other groups have experimented with subcutaneous methods of ice phase-change lipolysis, but used a −4.8° C. to −3.5° C. ice slurry comprising 0.9% sodium chloride and 10% glycerol. Upon knowledge and belief, as of January 2022, the United States Food and Drug Administration has only approved subcutaneous injection of small (i.e., sub-500 mg) quantities of glycerol. Dextrose-sodium chloride solutions, on the other hand, have a proven safety record and have been used in subcutaneous injection procedures for many decades. For example, subcutaneous injection of dextrose-sodium chloride solution is indicated for rehydration of acutely dehydrated patients. (See, e.g., Paula A. Rochon et al., *A systematic review of the evidence for hypodermoclysis to treat dehydration in older people*, J GERONTOL A, 1997 May; 52(3): M169-76; Tari Turner & Anne-Marie Cassano, *Subcutaneous dextrose for rehydration of elderly patients—an evidence-based review*, B.M.C. GERIATR 2004; 4(2).) The present disclosure provides a new and surprising improvement whereby a dextrose-sodium chloride solution may be used to form a safe and effective slurry.

In some embodiments of the slurry, the simple carbohydrate is dextrose and the salt is sodium chloride, both in aqueous solution, in sufficient concentrations such that the slurry may be super-chilled (i.e., at or below 0° C.) while remaining substantially free-flowing liquid solution.

The slurry may comprise about 5% wt ice, about 10% wt ice, about 15% wt ice, about 20% wt ice, about 25% wt ice, about 30% wt ice, about 35% wt ice, about 40% wt ice, about 45% wt ice, about 50% wt ice, about 55% wt ice, about 60% wt ice, about 65% wt ice, about 70% wt ice. The slurry may comprise about 5% vol ice, about 10% vol ice, about 15% vol ice, about 20% vol ice, about 25% vol ice, about 30% vol ice, about 35% vol ice, about 40% vol ice, about 45% vol ice, about 50% vol ice, about 55% vol ice, about 60% vol ice, about 65% vol ice, about 70% vol ice. In some embodiments, the slurry comprises about 40% wt ice. The ice: liquid ratio may be adjusted to provide any desired viscosity and or latent heat of phase change.

In any embodiment of the slurry, the slurry may be sterile. The liquid component may of the slurry be manufactured in sterile conditions, sealed in a sterile container, and opened by a medical practitioner at or near the time and/or place of care. Likewise, any apparatus, containers, surfaces, tubing, gloves, and/or skin to which the slurry is contacted may be sterile.

In an embodiment, the slurry comprises an aqueous solution of 12.2% dextrose and 0.18% sodium chloride in sterile water. In an embodiment, the slurry may comprise no drugs added to the slurry solution. Such solutions may be turned into a soft frozen ice slurry comprising about 40% ice and about 60% liquid aqueous solution using systems of the present disclosure.

In another aspect, the present description provides a surgical injection device comprising a container operably coupled to a surgical pump, wherein the container is operably coupled to a mixing means. In any embodiment, the container may contain a slurry, which may comprise a mixture of aqueous liquid and ice; the aqueously solution may comprise a monosaccharide and a salt; and the monosaccharide may be dextrose, and the salt may be sodium chloride. In an embodiment, the container may receive and contain a slurry comprising an aqueous solution of 12.2% dextrose and 0.18% sodium chloride in sterile water. In an embodiment, the slurry may comprise no drugs added to the slurry solution. The slurry may be a soft frozen ice slurry comprising about 40% ice and about 60% liquid aqueous solution.

In any embodiment of the surgical injection device, the container may comprise a bucket, bowl, pouch, screw-top container, or mix funnel. The container may be open-topped, or may comprise a sealable lid, or a may be permanently/semi-permanently sealed and comprise a fill valve. The container may be made from any suitable material. The container may be substantially rigid-bodied or may be substantially non-rigid. The container may be reusable, party reusable, single-use, or partly single-use. The mixing means may comprise one or more mix pumps or may comprise an augur. The mixing pumps may be fluidically coupled to the container by tubing, and the pumps may maintain the slurry in a state of circulation and/or agitation to prevent the slurry from solidifying and thereby maintain the desired liquid: ice ratio and consistency. In embodiments having an augur, the augur may rotate at a sufficient rate as to agitate and continually mix the slurry, allowing the slurry to be pumped properly. In some embodiments of the surgical injection device, the surgical pump may comprise a peristaltic roller pump.

Figure 5A:
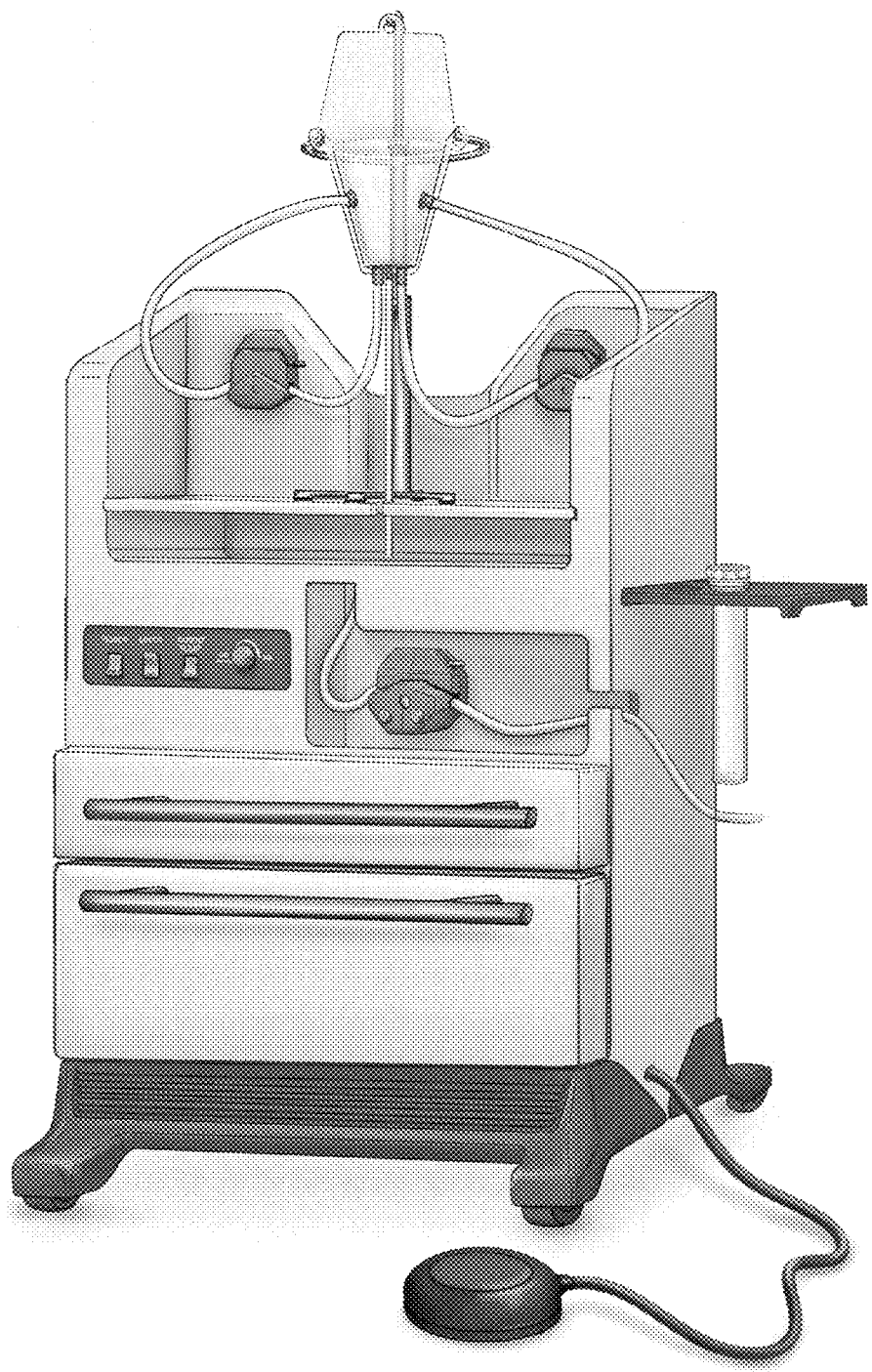
FIGS. 5A-5B depict exemplary perspective-view illustrations of an injection device according to the present disclosure.
Figure 5B:
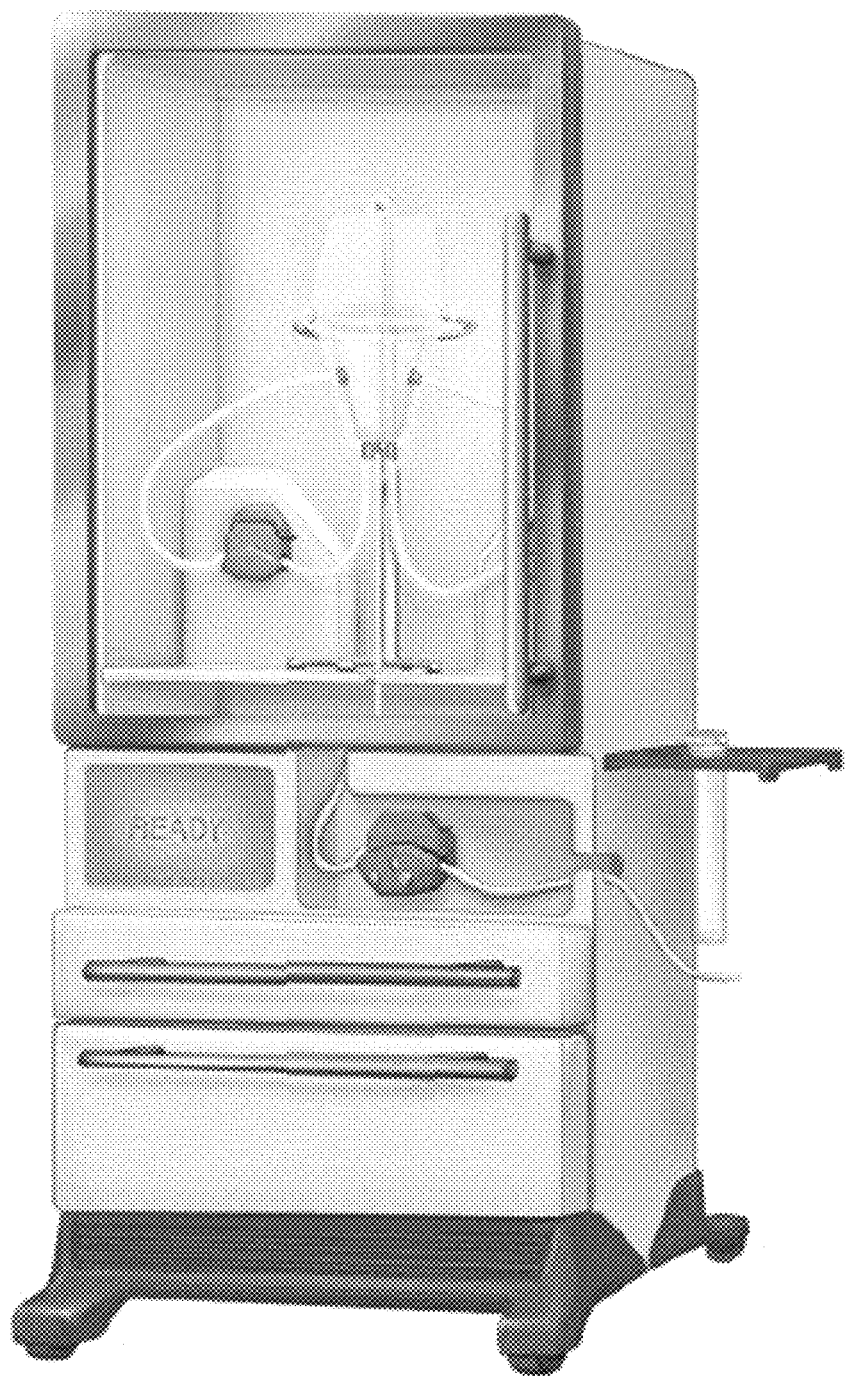
Figure 6:
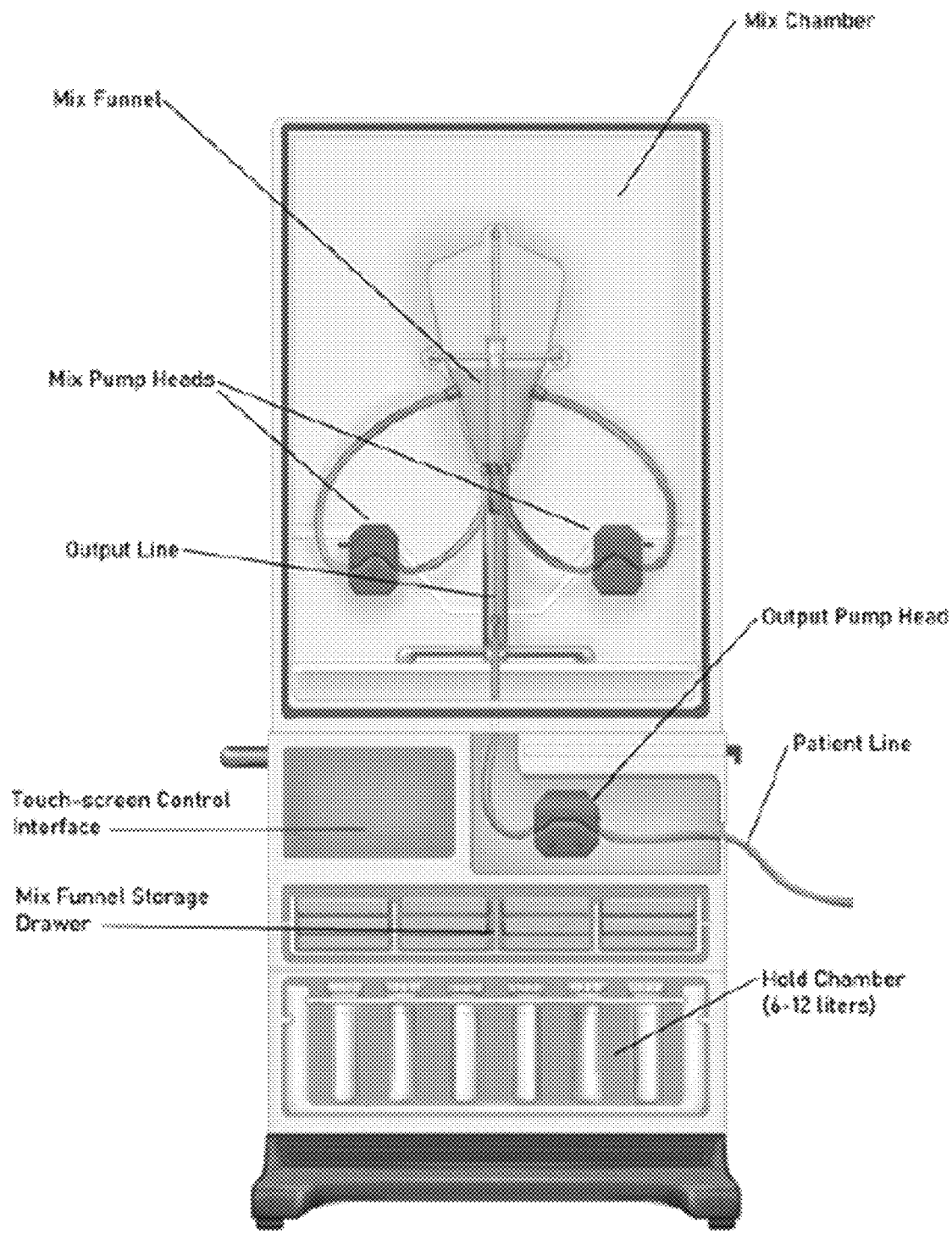
FIG. 6 depicts an exemplary cut-away diagram of an injection device according to the present disclosure. An exemplary embodiment such as depicted in FIG. 6 is further elaborated in the Examples, infra.
Figure 7:
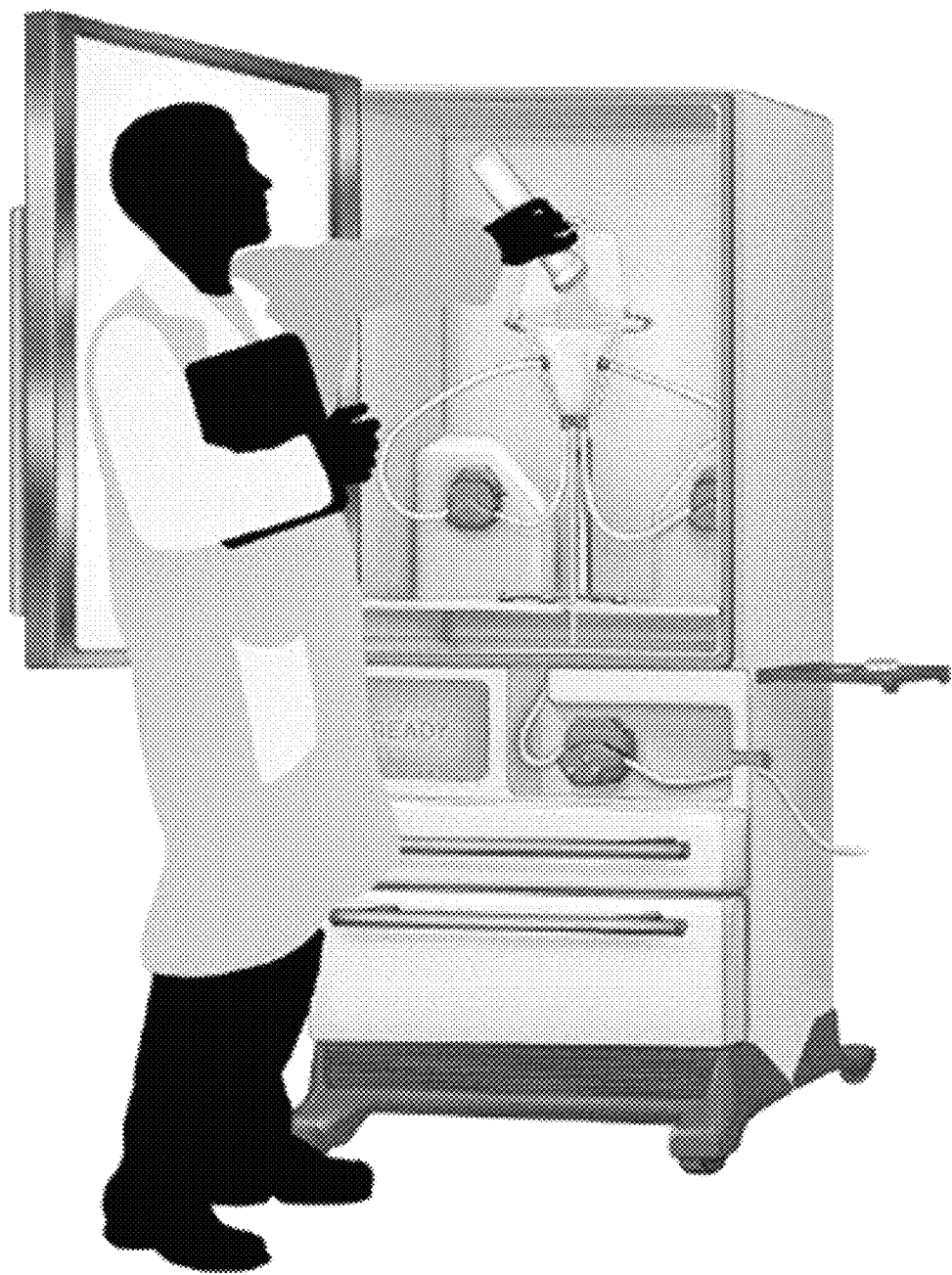
FIG. 7 depicts an exemplary illustration of a qualified medical practitioner pouring slurry comprising dissolved simple carbohydrate and dissolved salt into a mix funnel of an exemplary embodiment of the devices and systems of the present disclosure (such as the device illustrated in FIG. 6). The slurry may be prepared from an aqueous solution that may be premixed by a third party manufacturer, and may be delivered and kept sterile in liquid phase. A qualified medical practitioner may pour the solution into a receptacle of a devices and systems of the present disclosure or a companion device that cools the solution and mixes it will ice, creating a slurry of, for example, about 60 percent liquid solution and 40 percent solid ice. The devices and systems of the present disclosure may maintain the slurry at appropriate temperature and constituency, e.g., by means of a cooling system and augur mechanism.
Figure 8:
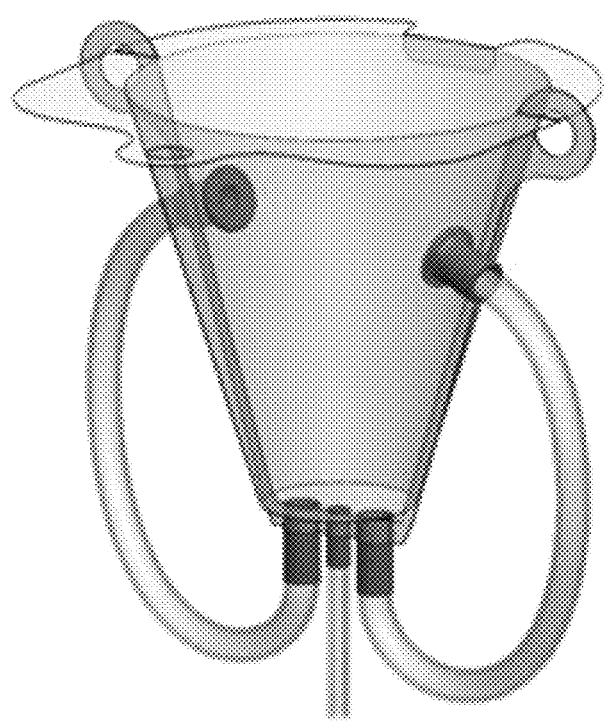
FIG. 8 depicts an exemplary illustration of an embodiment of a mix funnel for use in embodiments of the devices and systems of the present disclosure. The mix funnel in the illustration has three tubing outlets, which may be coupled with tubing. The tubing may be in fluidic communication with, e.g., mix pumps. The tubing may be in fluidic communication with an outlet pump, and further in fluidic communication with cannula or instillation needle used to introduce slurry into a subject's body.
Figure 9:
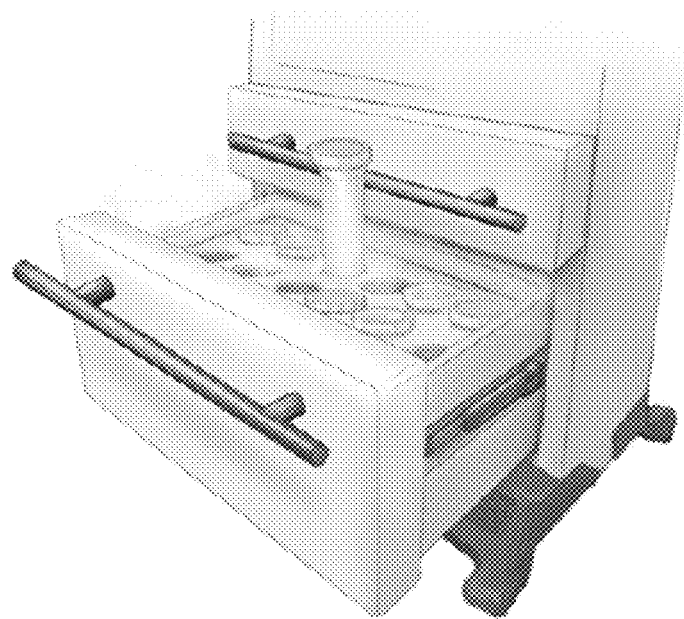
FIG. 9 depicts an exemplary embodiment of a hold chamber of an embodiment of the devices and systems of the present disclosure. The hold chamber may hold aqueous solution and/or slurry; or may hold one or more containers containing aqueous solution and/or slurry. The hold chamber may refrigerate its contents, for example, maintaining aqueous solution at cool temperature for preservation, or for maintaining slurry at a freezing temperature to maintain ice content and consistency.
Figure 10:
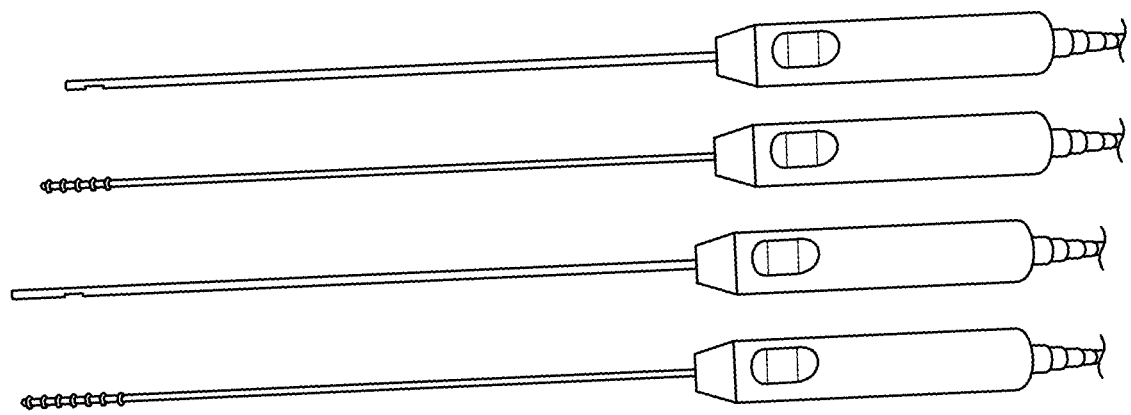
FIG. 10 is an overhead photograph of exemplary cannulae/instillation needles that may be used for the surgical injection, through an incision, of ice slurry into a subject's body.
Figure 11:
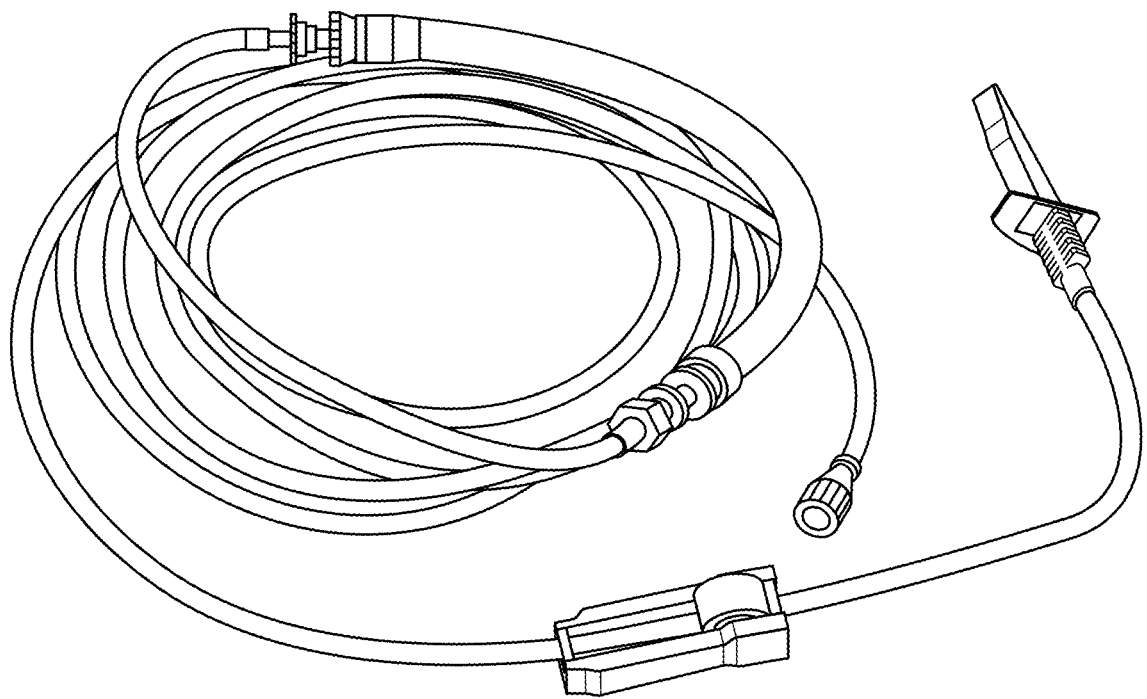
FIG. 11 is a perspective-view photograph of exemplary single-use sterile tubing that may be used in the methods, systems, and devices of the present disclosure.

The surgical injection device, in an exemplary embodiment, may include the following components: a main unit, including a mix chamber (mix funnel, mix pump heads), output lines, patient line, mix funnel storage drawer, foot pedal, and hold chamber (FIG. 5A), and, optionally, an electronic user interface such as, e.g., a touchscreen (FIG. 5B). More particularly, the mix chamber will house the funnel, mix pump heads and output line (FIG. 6); the funnel unit is a specially designed sterile single-use mixing bag that includes connections to three lines of tubing: two lines of tubing pass through two peristaltic pumps (mix pump heads) and one line of tubing passes through an output pump head, and the slurry solution is added to the device by placing the slurry into the funnel unit (FIG. 8); the optional touchscreen (FIG. 5B) is a user control interface for controlling the mixing pumps as well as the rate of output pump, while the foot pedal turns the output pump on/off; and the hold chamber holds 6-12 liters of slurry in reusable sterile cannister (FIG. 9). The aqueous solution (exemplarily comprising dextrose and sodium chloride) used to form the slush may be manufactured by a third party and provided to the end-user. When the sterile aqueous solution is added to the device, the device makes a soft injectable frozen ice slurry to be used in phase-change lipolysis treatment(s) (FIG. 7).

As stated supra, the exemplary device embodiment includes a reusable cannister, which will be filled with sterile aqueous solution (e.g., comprising dextrose and sodium chloride). The cannister may be filled and sealed at an off-site manufacturing facility, or may be filled and sealed on-site, at the same facility as the point of care. The reusable cannister and its contents may be kept at an above-freezing temperature, e.g., at room temperature or refrigerated. The cannister may be opened/unsealed at or near the time and/or place of care. The sterile aqueous solution may be transformed into slurry using a freezer device at the point of care. The freezer device may be a component of the surgical injection device that is fluidically coupled to the device container, such that the freezer device freezes the aqueous solution into soft frozen ice slurry and feeds the slurry into the surgical injection device container. Alternatively, the freezer device may be external to the injection device, such that the freezer device freezes the sterile aqueous solution, and the output sterile soft frozen ice slurry may then be manually transferred using accepted sterile operating room procedures to the device funnel unit (a sterile single use mixing bag) (FIG. 7). The funnel unit may be manufactured in accordance with a proprietary design compatible with the devices and systems of the present disclosure. In an exemplary embodiment, the funnel unit is connected via a smaller third tube (see FIG. 8) to an output pump head (e.g., a peristaltic pump). Single-use sterile patient tubing is connected between the funnel unit and the patient administration cannula (FIG. 6). The sterile cannula is used to inject the slurry into the patient's body. The surgical injection device maintains the temperature of the sterile slurry until it is injected (FIG. 7). (Once the slurry is instilled into the patient's body, the slurry melts and therefore at this point there is no need to control the temperature of the slurry.) The device may comprise cannulae/instillation needles (FIG. 12) and single-use tubing (FIG. 13).

In any embodiment of the surgical injection device, the device may further comprise an instillation needle, the needle operably coupled to the surgical pump. In some embodiments, the needle is a 2.7 mm OD needle.

In any embodiment of the surgical injection device, the container may further comprise a lid enclosing the container.

In another aspect, the present disclosure provides a surgical injection system, the system comprising a container, wherein the container is configured to receive and contain slurry; a surgical pump operably coupled to the container; and an instillation needle operably coupled to the surgical pump; wherein the slurry comprises a chilled aqueous solution and ice, wherein the aqueous solution comprises dissolved monosaccharide and dissolved salt.

In some embodiments, the container comprises a mix funnel. (See, e.g., FIG. 6) The mix funnel may further comprise a mixing means or may be operably coupled with a mixing means. The mixing means may agitate the slurry to maintain a preferred liquid: ice ratio and consistency. In some embodiments, the mix funnel comprises an upper portion and a lower tip portion. In such embodiments, the upper portion of the mix funnel may be fluidically coupled by one or more connections to tubing to a mixing means. The mixing means may comprise one or more mixing pumps. In some embodiments, the mix funnel may further comprise an internal augur.

In some embodiments of the surgical injection system, the monosaccharide is dextrose and the salt is sodium chloride. In some embodiments, the system is capable of effective operation at supercooled temperatures. In some embodiments, the slurry is at a sufficiently cold temperature such that the slurry can cause ice phase-change lipolysis when contacted with live mammalian fat cells. In some embodiments, the mammalian subject's live fat cells may be reduced to at or below 10° C. In some embodiments, the slurry may comprise an aqueous solution comprising 12.2% dextrose and 0.18% sodium chloride in sterile water. In some embodiments, the slurry may comprise no drugs added. In some embodiments, the slurry may comprise an aqueous solution comprising 12.2% dextrose and 0.18% sodium chloride in sterile water, with no drugs added. The slurry may be a soft frozen ice slurry comprising about 40% ice and about 60% liquid aqueous solution.

In some embodiments, the container may be substantially surrounded by a cooling element, configured to maintain the contents of the container at a slurry operating temperature. In any embodiment, the slurry operating temperature may be in a temperature range from about −10° C. to slightly greater than 0° C. In any embodiment, the slurry operating temperature may be about 0° C., about −5° C., about −8° C., or about −10° C.

In some embodiments, the surgical injection system may further comprise a refrigeration chamber or "hold chamber". The hold chamber may be or may not be operably or fluidically coupled to the container. In embodiments wherein the hold chamber is not operably or fluidically coupled to the container, a qualified practitioner may transfer solution and/or slurry to and from the hold chamber. In embodiments wherein the hold chamber is operably and/or fluidically coupled to the container, the system may transfer solution and/or slurry to and from the hold chamber via a pumping means. The hold chamber may be configured to maintain its contents at a slurry operating temperature. The hold chamber may be configured to receive ice slurry from the container, emptying the container and permitting the introduction of ingredients for the preparation of another batch of slurry. Thus, a batch of slurry may be maintained in the refrigeration chamber while, concurrently, another batch of ice slurry may be prepared. In some embodiments, the hold chamber may comprise one or more receptacles for receiving slurry cannisters, which may have sidewalls comprising a Teflon™ material. In any such embodiment, the preparation of a batch of slurry may take about 50 minutes. In any embodiment, the slurry operating temperature may be in a temperature range from about −10° C. to slightly greater than 0° C. In any embodiment, the slurry operating temperature may be about 0° C., about −1° C., about −2° C., about −3° C., about −4° C., about −5° C., about −6° C., about −7° C., about −8° C., about −9° C., or about −10° C. In any embodiment, the slurry operating temperature may be precisely 0° C., −1° C., −2° C., −3° C., 4° C., −5° C., −6° C., −7° C., −8° C., −9° C., −10° C., or lower temperature.

In another aspect, the present disclosure provides a method of causing ice phase-change lipolysis in a mammalian subject comprising the steps of: subcutaneously injecting a slurry such that the slurry comes into proximity with fat cells to be ice-phase-lipolysed, wherein the slurry comprises a mixture of chilled aqueous solution and ice, wherein the aqueous solution comprises dissolved simple carbohydrates and dissolved salt.

In some embodiments, the dissolved simple carbohydrates consist of dextrose and dissolve salt consists of sodium chloride. In some embodiments, the aqueous solution comprises 12.2% wt dissolved dextrose and 0.18% wt dissolved sodium chloride. In some embodiments, the slurry comprises 60% liquid aqueous solution and 40% ice.

In any embodiment of the method, the method may be performed using the devices and systems provided in the present disclosure supra. In any embodiment of the method, the method may be performed using sterile devices and materials, and aseptic techniques.

In any embodiment of the method, the method may be performed when the subject is awake and without general anesthesia. In any embodiment, the subject may be a male or female human adult (i.e., 18 years of age or older).

EXAMPLES

1. Exemplary Method Protocol

In an exemplary non-limiting example of using of the materials, systems, and methods of the present disclosure, a qualified medical professional, using a cannula, administers sterile soft-frozen ice slurry subcutaneously into a human patient's areas of localized adipose tissue. Exposure of adipose cells to cold causes cell death. Over time, the slurry and cells are absorbed and excreted from the patient's body. The protocol used in ice phase-change lipolysis is substantially identical to the first step of conventional liposuction, in that both processes begin by instilling a solution subcutaneously. In the case of liposuction, a tumescent solution (usually comprising saline, epinephrine to constrict blood vessels, and lidocaine to control pain) is typically instilled into the patients, typically in a volume equal to the amount of fat removed, though the amount may vary. (See Ingargiola M. et al., *Cryolipolysis for Fat Reduction and Body Contouring: Safety and Efficacy of Current Treatment Paradigms*. PLAST AND RECONST SURG, June 2015 135(6) 1581-90.)

More particularly, the exemplary procedure follows the steps of:
(1) prepare the human patient's skin as usual per a surgical procedure (e.g., betadine, chlorhexidine, etc.).
(2) inject local anesthetic into the insertion sites. The cold temperature of the sterile slurry inactivates many local sensory nerves, but some nerves, especially pressure sensing nerves, may remain active during the procedure. Therefore, local anesthetic is recommended.
(3) Determine the rate or infusion of the sterile slurry, which would typically be from 200 mL to 400 mL per minute.
(4) Make an incision at the insertion site(s) and infuse the sterile slurry through the anesthetized incisions using a cannula to treat the desired areas. The sterile slurry is added until the treated areas are tumesced and some firmness is noted. A typical slurry injection would be about 2 liters to about 4 liters in volume.
And (5) close the incisions with sutures, if desired, and place pads to absorb any leakage that the patient experiences.

Following such procedure, the patient may experience some drainage of fluid from the insertion site(s) for up to several days. The patient may experience redness, bruising, or tenderness at the insertion site for up to several weeks.

2. Mode of Device Operation

As an exemplary, non-limiting example of a mode of user operation of the devices and systems of the present disclosure, the device has 4 modes of operation, START-UP, STAND-BY, ACTIVE, and PUMP ONLY. When the user powers on the unit, it will go into a START-UP mode, during which the interactive touchscreen display will light up and the cooling system activate. Touchscreen buttons on the controller will allow the user to toggle between the various modes.

START-UP: When the unit is powered on, the temperature will approach 0° C. in the START-UP mode.

STAND-BY: The STAND-BY mode keeps the temperature at 0° C. for optimal levels for patient treatment.

ACTIVE: The ACTIVE mode will start the mix pump heads in the mix chamber and prepares the output pump head (which may also be referred to as the "patient pump") for use when the physician depresses the foot pedal. (FIG. 5A).

PUMP ONLY: The PUMP ONLY mode prepares the output pump head (also known as the patient pump) for use. (FIG. 5A).

3. Clinical Pilot Study

The slurry, device, and system of the present disclosure were tested in a five-person trial. The materials and methods all met professional and ethical standards, and the trial patients provided fully informed consent to the procedures.

The test subjects consisted of five adult women seeking abdominoplasty surgery, each having excess fat in the subcutaneous space of the lower abdomen. By selecting test subjects who were undergoing abdominoplasty, if any complications were to arise, the skin could be removed as part of the cosmetic procedure for which the test patients were already scheduled. Further, the abdominoplasty procedures permitted the removal of dermal tissue for histological examination. A preoperative ultrasound was performed to assess the fat tissue.

A sterile ice slurry at about 0° C. comprising dextrose and sodium chloride was prepared using the devices and methods described in the present disclosure. The slurry was placed in the container and mixed with an auger. The slurry was then pumped from the container to the cannula/instillation needle using a roller pump.

Subjects were locally anaesthetized with nitrous oxide pain management. A surgeon inserted an instillation needle into the subcutaneous space of the right lower abdomen and administered a volume of 300 cc-500 cc sterile ice slurry into the right lower abdominal subcutaneous space using sterile conditions. The left lower abdomen area was intentionally untreated, as a negative control.

The procedure was out-patient. Test subjects tolerated the procedure well, and subjects were sent home immediately following the procedure.

Figure 4A:
FIGS. 4A-4B are photographs depicting excised subcutaneous lower-abdominal fat tissue from a test subject who underwent the method of the present disclosure.
Figure 4B:
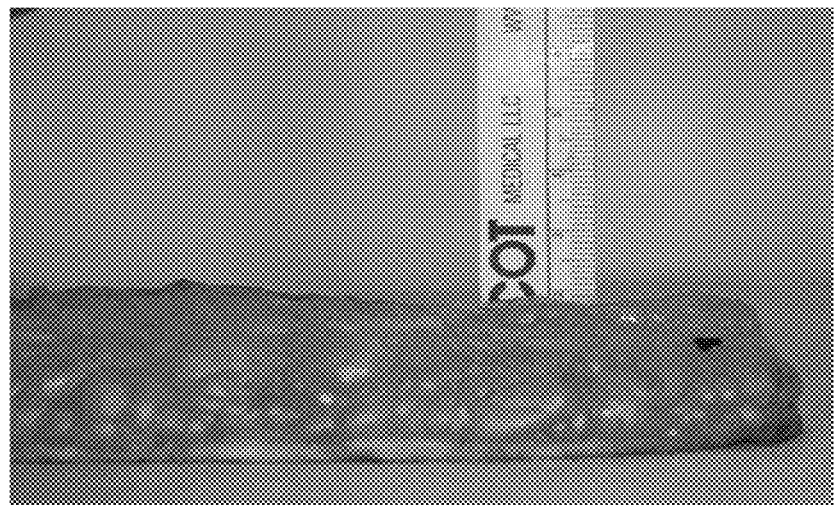

Tissue specimens were taken between 1 and 16 weeks later, at the time of the test subject's already-scheduled abdominoplasty operation. At that time, abdominal tissue was harvested and photographs taken. (FIGS. 4A-4B.) Specimens from the right lower abdomen (test area) and left lower abdomen (negative control) were sent for histology. The trial patients demonstrated some cellular changes. Specifically, the treated fat tissue showed higher rates of cell death and loss of volume than untreated negative control.

4. Proposed Clinical Testing.

The following clinical research proposal is a non-limiting prophetic example.

To evaluate further the safety and efficacy of the systems and methods of the present disclosure in the minimally invasive treatment of excessive fat in the submental area and in the arms, chest, abdomen, flanks, torso, back, thighs, and legs, the following research protocol is proposed:

The clinical study will be conducted in compliance with Good Clinical Practice (GCP) and other requirements for an investigational device study as set forth in 21 C.F.R. Parts 50, 54, 56, and 812, to the extent applicable. At least 30 subjects will be enrolled across at least two different clinical sites. Since the device's instillation of slurry into subcutaneous spaces is not dependent on the area of the body (i.e., all areas for of the body are administered subcutaneously) for reduction of fat, the study endpoint will not necessarily depend on body area.

The primary safety endpoint will be the incidence of unanticipated adverse device effects. The anticipated adverse device effects of the methods and systems of the present disclosure may include redness, bruising, or tenderness. The primary efficacy endpoint will involve a discernible fat layer reduction. The secondary endpoint will be assessed by a questionnaire administered at 12 weeks post treatment. The questionnaire will assess the comfort of the procedure, how satisfied the participant was with results, and whether the participant will recommend the procedure to a friend.

A usability questionnaire will also be completed by the clinical investigators (i.e., physicians) to assess the ease of use of the device interface and assess its associated labeling.

As used herein, the term "about" refers to at least ±10%.

The word "exemplary" is used herein to mean "serving as an example, instance, or illustration." Any embodiment described as "exemplary" is not necessarily to be construed as preferred or advantageous over other embodiments, or to exclude the incorporation of features from other embodiments.

Whenever a numerical range is indicated herein, it is meant to include any cited numeral (fractional or integral) within the indicated range. Moreover, it is meant to be inclusive of the number defining the range, e.g., a range given as from 1 to 10 includes all numbers between 1 and 10, as well as the numbers 1 and 10. It should be further understood that the description in range format is merely for convenience and brevity and should not be construed as an inflexible limitation on the scope of the disclosure. Accordingly, the description of a range should be considered to have specifically disclosed all the possible subranges as well as individual numerical values within that range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

Those in the art will understand that a number of variations may be made in the disclosed aspects and embodiments, all without departing from the scope of the invention, which is defined solely by the appended claims.

The invention claimed is:

1. A method of causing ice phase-change lipolysis in a mammalian subject, the method comprising subcutaneously injecting a slurry of chilled aqueous solution and ice such that the slurry comes into proximity with fat cells to be ice-phase-lipolysed, wherein the injecting is performed using an injection device comprising:
   a sterile, single-use funnel-shaped container configured to receive and contain a slurry and comprising a lid for sealing the container;
   a mixing means coupled to the container comprising
      one or more mixing tubes, wherein each end of each mixing tube is attached to the container, and wherein one end of each mixing tube is attached to the container at a lower end thereof, and
      one or more mixing pumps associated with each mixing tube and configured to circulate the slurry from the container through each mixing tube to agitate the slurry, and wherein one or more mixing pumps is a peristaltic pump;
   a patient tube operably coupled to the container;
   a roller pump operably coupled to the container to facilitate administering the slurry from the container to a patient via the patient tube, and wherein the roller pump is a peristaltic roller pump;
   a cannula or an instillation needle operably coupled to the roller pump via the patient tube to introduce the slurry to a patient; and
   wherein the mixing means is configured to agitate the slurry, thereby maintaining a predetermined liquid-ice ratio and/or consistency.

2. The method of claim 1, wherein the aqueous solution becomes the slurry when cooled to a temperature of or below about −1.5° C. while remaining a substantially free-flowing liquid solution mixture.

3. The method of claim 1, wherein the aqueous solution comprises a dissolved monosaccharide and a dissolved salt.

4. The method of claim 3, wherein the monosaccharide is dextrose and the salt is sodium chloride.

5. The method of claim 1, wherein the slurry is injected at a temperature between about −0.5° C. and about −1.7° C.

6. A method of reducing bodyfat in a patient in need of bodyfat reduction intervention, comprising the method of claim 1 such that the slurry comes into proximity with bodyfat to be reduced.

* * * * *